US006485924B2

(12) United States Patent
Mendoza et al.

(10) Patent No.: US 6,485,924 B2
(45) Date of Patent: Nov. 26, 2002

(54) METHOD FOR IDENTIFYING INHIBITORS OF CYTOKINESIS

(75) Inventors: Manuel Mendoza, Vienna (AT); Michael Glotzer, Vienna (AT)

(73) Assignee: Boehringer Ingelheim International GmbH (DE)

( * ) Notice: Subject to any disclaimer, the term of this patent is extended or adjusted under 35 U.S.C. 154(b) by 0 days.

(21) Appl. No.: 09/730,568

(22) Filed: Dec. 7, 2000

(65) Prior Publication Data

US 2001/0018196 A1 Aug. 30, 2001

Related U.S. Application Data

(60) Provisional application No. 60/175,157, filed on Jan. 7, 2000.

(30) Foreign Application Priority Data

Dec. 7, 1999 (EP) ............................................ 99124354

(51) Int. Cl.$^7$ ........................... C12Q 1/42; C12Q 1/34; C12Q 1/00

(52) U.S. Cl. ............................. 435/21; 435/18; 435/4

(58) Field of Search ............................ 435/21, 18, 4

(56) References Cited

PUBLICATIONS

Beites, C.L. et al., "The septin CDCrel–1 binds syntaxin and inhibits exocytosis," Nature Neurosci. 2:434–439, Nature America Inc. (May 1999).
Bi, E. et al., "Involvement of an Actomyosin Contractile Ring in Saccharomyces cerevisiae Cytokinesis," J. Cell Biol. 142:1301–1312, The Rockefeller University Press (Sep. 1998).
Byers, B. and L. Goetsch, "A Highly Ordered Ring of Membrane–Associated Filaments in Budding Yeast," J. Cell Biol. 69:717–721, The Rockefeller University Press (1976).
Chant, J. et al., "Role of Bud3p in Producing the Axial Budding Pattern of Yeast," J. Cell Biol. 129:767–778, The Rockefeller University Press (1955).
Cooper, J.A. and D.P. Kiehart, "Septins May Form a Ubiquitous Family of Cytoskeletal Filaments," J. Cell Biol. 134:1345–1348, The Rockefeller University Press (1996).
DeMarini, D.J. et al., "A Septin–based Hierarchy of Proteins Required for Localized Deposition of Chitin in the Saccharomyces cerevisiae Cell Wall," J. Cell Biol. 139:75–93, The Rockefeller University Press (1997).
Field, C.M. et al., "A Purified Drosophila Septin Complex Forms Filaments and Exhibits GTPase Activity," J. Cell Biol. 133:605–616, The Rockefeller University Press (1996).
Field, C.M. and D. Kellogg, "Septins: cytoskeletal polymers or signalling GTPases?," Trends Cell Biol. 9:387–394, Elsevier Science (Oct. 1999).

Ford, S.K. and J. R. Pringle, "Cellular Morphogenesis in the Saccharomyces cerevisiae Cell Cycle: Localization of the CDC11 Gene Product and the Timing of Events at the Budding Site," Developemental Genetics 12:281–292, Wiley–Liss, Inc. (1991).
Frazier, J.A. et al., "Polymerization of Purified Yeast Septins: Evidence That Organized Filament Arrays May Not Be Required for Septin Function," J. Cell Biol. 143:737–749, The Rockefeller University Press ( Nov. 1998).
Haarer, B.K. and J.R. Pringle, "Immunofluorescence Localization of the Saccharomyces cerevisiae CDC12 Gene Product to the Vicinity of the 10–nm Filaments in the Mother–Bud Neck," Mol. Cell. Biol. 7:3678–3687, American Society for Microbiology (1987).
Hartwell, L.H., "Genetic Control of the Cell Division Cycle in Yeast. IV. Genes Controlling Bud Emergence and Cytokinesis," Exper. Cell Res. 69:265–276, The International Society for Cell Biology (1971).
Hazlett, T.L. et al., "Solution Dynamics of $p21^{ras}$ Proteins Bound with Fluorescent Nucleotides: A Time–Resolved Fluorescence Study," Biochem. 32:13575–13583, American Chemical Society (1993).
Hsu, S.–C. et al., "Subunit Composition, Protein Interactions, and Structures of the Mammalian Brain sec6/8 Complex and Septin Filaments," Neuron 20:1111–1122, Cell Press (Jun. 1998).
Kim, H.B. et al., "Cellular Morphogenes is in the Saccharomyces cerevisiae Cell Cycle: Localization of the CDC3 Gene Product and the Timing of Events at the Budding Site," J. Cell Biol. 112:535–544, The Rockefeller University Press (1991).
Kinoshita, M. et al., "Nedd5, a mammalian septin, is a novel cytoskeletal component interacting with actin–based structures," Genes & Develop. 11:1535–1547, Cold Spring Harbor Laboratory Press (1997).
Kirschner, M. and T. Mitchison, "Beyond Self–Assembly: From Microtubules to Morphogenesis," Cell 45:329–342, Cell Press (1986).
Kouyama, T. and K. Mihashi, "Fluorimetry Study of N–(1–Pyrenyl)iodoactemide–Labelled F–Actin. Local Structural Change of Actin Protomer both on Polymerization and on Binding of Heavy Meromyosin," Eur. J. Biochem. 114:33–38, Springer–Verlag (1981).
Longtine, M.S. et al., "The septins: roles in cytokinesis and other processes," Curr. Opin. Cell. Biol. 8:106–119, Current Biology Ltd. (1996).

(List continued on next page.)

Primary Examiner—Ralph Gitomer
Assistant Examiner—Mahreen Chaudhry
(74) Attorney, Agent, or Firm—Stern, Kessler, Goldstein & Fox P.L.L.C.

(57) ABSTRACT

Method for identifying compounds that inhibit cytokinesis, wherein the compounds are tested for their ability to modulate the formation and/or the stability of septin filaments. The compounds are useful in tumor therapy.

48 Claims, 9 Drawing Sheets

PUBLICATIONS

Longtine, M.S. et al., "Role of the Yeast Gin4p Protein Kinase in Septin Assembly and the Relationship between Septin Assembly and Septin Function," *J. Cell Biol.* *143*:719–736, The Rockefeller University Press (Nov. 1998).

Lupas, A. et al., "Predicting Coiled Coils from Protein Sequences," *Science 252*:1162–1164, American Association for the Advancement of Science (1991).

Mitchison, T. and M. Kirschner, "Microtubule assembly nucleated by isolated centrosomes," *Nature 312*:232–237, Macmillan Publishers Ltd. (1984).

Mitchison, T.J., "Compare and Contrast Actin Filaments and Microtubules," *Mol. Biol. Cell 3*:1309–1315, The American Society for Cell Biology (1992).

Neufeld, T.P. and G.M. Rubin, "The Drosophila *peanut* Gene Is Required for Cytokinesis and Encodes a Protein Similar to Yeast Putative Bud Neck Filament Proteins," *Cell 77*:371–379, Cell Press (1994).

Sanders, S.L. and I. Herskowitz, "The Bud4 Protein of Yeast, Required for Axial Budding, Is Localized to the Mother/Bud Neck in a Cell Cycle–dependent Manner," *Cell Biol. 134*:413–427, The Rockefeller University Press (1996).

Self, A.J. and A. Hall, "Measurement of Intrinsic Nucleotide Exchange and GTP Hydrolysis Rates," *Methods in Enzymology 256*:67–76, Academic Press, Inc. (1995).

Xie, H. et al., "Characterization of the Mammalian Septin H5: Distinct Patterns of Cytoskeletal and Membrane Association From Other Septin Proteins," *Cell Motility and The Cytoskeleton 43*:52–62, Wiley–Liss Inc. (Apr. 1999).

METHOD FOR IDENTIFYING INHIBITORS OF CYTOKINESIS

The present application claims the benefit of U.S. Appl. Ser. No. 60/175,157, filed Jan. 7, 2000, which is herein incorporated by reference, and EP 99 124 354,4, filed Dec. 7, 1999, which is herein incorporated by reference.

The present invention relates to a therapy interfering with cell division, in particular tumor therapy.

The septins are an evolutionary conserved family of proteins required for cytokinesis (reviewed in Cooper and Kiehart, 1996); Longtine et al., 1996; Field and Kellogg 1999). The septins were first described in S. cerevisiae, where mutants in any of the genes CDC3, 10, 11 and 12 are unable to complete cytokinesis, giving rise to multinucleate cells (Hartwell, 1971). Sequence analysis of these four genes by Pringle and co-workers (GenBank accession numbers L16548-L16551) revealed that they encode proteins with similar primary structure, defining the septin family. The known septins range in size from 30 to 60 kDa and contain sequences characteristic of the GTPase superfamily of proteins. In yeast, the septins localize at the site of bud emergence, and indirect but compelling evidence indicates that the septins are components of the neck filaments, a structure previously described by electron microscopy as an ordered array of filaments in close association with the membrane of the bud (Byers and Goetsch, 1976). Neck filaments have only been observed in yeast cells so far. However, and in spite of the differences in the mechanism of cytokinesis between yeast and animal cells, septins were later found to be widespread in higher eukaryotes. A Drosophila septin mutant, pnut, is defective in cytokinesis, and the Peanut protein localizes to the cleavage furrow of dividing cells (Neufeld and Rubin, 1994). Septins with similar localization patterns have also been described in amphibia and mammals (Kinoshita et al., 1997; Xie et al., 1999), and inactivation of septin function by antibody microinjection in cultured mammalian cells and in Xenopus embryos results in cytokinesis defects (Kinoshita et al., 1997; Xie et al., 1999)). Thus, it appears that the septins are involved in an aspect of cell division that has been conserved from yeast to animal cells. Several yeast proteins required for cytokinesis and bud site selection are recruited to the cell division site in a septin-dependent manner (Chant, et al., 1995; Sanders and Herskowitz 1996; DeMarini et al., 1997; Bi et al., 1998), suggesting that the septins can work as a scaffold that directs the correct localization of other proteins. However, the molecular mechanism of septin function in animal cells is still unclear.

Biochemical experiments have revealed that the septins exist as an heteromultimeric complex containing three (in Drosophila), four (in yeast) or more (in mammals) different septin polypeptides (Field et al., 1996; Frazier et al., 1998; Hsu et al., 1998). Moreover, septin complexes can be purified in a filamentous state (Field et al., 1996; Frazier et al., 1998; Hsu et al., 1998). Thus, it is likely that the septins can form filaments in vivo, even if septin-containing filamentous structures (like the neck filaments in yeast) have not yet been described in animal cells. The mechanism and regulation of septin filament assembly remain nevertheless mysterious, as well as many of the physico-chemical properties of the filaments. For instance, it is not known whether the coiled coil domain is involved in polymerization, or whether septin filaments are polar structures. Several septin proteins have been shown to bind, or bind and hydrolyse, guanine nucleotide (Kinoshita et al., 1997; Field et al., 1996; Beites et al., 1999), and mutations that inhibit nucleotide binding also affect septin localization in mammalian cells (Kinoshita et al., 1997; Field et al., 1996). Inter alia, it was shown that the GTP-binding activity of the mammalian septin Nedd5 is necessary for its normal localization (Kinoshita et al., 1997).

However, the precise role of GTP (guanosine triphosphate) binding and hydrolysis in filament formation has not been elucidated.

It was an object of the invention to elucidate the mechanisms involved in septin filament formation in order to provide a novel approach for therapy, in particular cancer therapy, that is based on modulating septin filament formation and thus interfering with cytokines is.

To solve the problem underlying the present invention, septin filament assembly was reconstituted in vitro using a recombinant septin. It was shown that a septin protein can assemble into filaments in a nucleotide-dependent fashion, and that these polymers, like actin filaments and microtubules, are polar structures that assemble with a nucleation mechanism.

The results obtained in the experiments of the present invention show that GTP binding and hydrolysis regulate the filament assembly of a septin protein, in addition, they present a kinetic analysis of septin polymerization.

Thus, the present invention provides the first direct evidence of nucleotide-dependent filament assembly of a septin protein. Based on these observations, it may also be assumed that XSepA filaments assemble with a nucleation mechanism, and that filament growth and stability is regulated by the state of bound guanine nucleotide. In addition, due to the similarity of the septin, both on the sequence level and in terms of their function, it may be assumed that an essentially identical mechanism operates at the level of heteromultimeric septin filaments.

Kinetic analysis of the polymerization reaction has revealed the existence of a lag phase in septin filament assembly FIG. 4A. This feature is indicative of nucleated polymerization, whereby initiation of filaments is energetically unfavored, but under sufficiently high monomer concentrations, nuclei can form. Addition of monomers to these nuclei to yield long filaments subsequently takes place with a higher association constant than the one required for filament initiation (Cantor and Schimmel; 1980)). Actin and tubulin follow such a polymerization mechanism. The existence of a critical concentration (the concentration below which polymerization cannot occur) is a consequence of the kinetic barrier to nucleation. As shown in FIG. 4B, a critical concentration of approximately 0.5 mg/ml, or ~12 $\mu$M (in comparison with ~0.2 $\mu$M for actin (Mitchison, 1992), or 14 $\mu$M for pure tubulin in glycerol buffer (Mitchison and Kirschner, 1984) for XSepA polymerization exists. These data indicate that XSepA filaments are nucleated polymers. On the other hand, a mechanism of linear polymerization (where monomers associate end-to-end with an affinity constant independent of polymer length) has been proposed for septin filaments, based on the length distribution of immunopurified septin complexes (Field et al., 1996); Frazier et al., 1998). It is very likely, however, that in the absence of polymer-stabilising conditions long filaments would not have survived the purification procedure. This could be due to simple mechanical breakage and/or to depolymerization caused by either depletion of nucleotide, or to effects of dilution of the septin complex below the putative critical concentration. In fact, only short filaments (up to 350 nm) were observed in these cases (Field et al., 1996; Frazier et al. 1998) rendering ambiguous a kinetic interpretation of length distribution data.

Two additional properties of actin filaments and microtubules seem to be shared by XSepA filaments. The polymerization dynamics of XSepA in the presence of the slowly hydrolysable GTP analogue, GTP-γ-S suggest a role of nucleotide hydrolysis in the destabilisation of the filament structure (FIGS. 4A–4C). Likewise, a number of experimental approaches has established that NTP hydrolysis is linked to destabilisation of the microtubule and actin filament lattices (Mitchison, 1992). Another important feature of these cytoskeletal elements is filament polarity, since it plays a key role in the organization of higher order structures and in the directional transport of molecules along filamentous tracks (Mitchison, 1992); Kirschner and Mitchison, 1986). Using fluorescence microscopy to visualise elongation of pre-assembled septin filaments, it could be observed that the two ends grow with different kinetics (FIGS. 5A and 5B). Although these data provide a strong indication of polarity in septin filaments, proper determination of the growth rates at the different ends could not be achieved. Further analysis of the elongation process is still needed, together with high-resolution structural studies of the septin filaments.

It is interesting to compare the structural features of in vitro-assembled XSepA filaments with those of septin filaments purified from yeast or animal cells. The diameter of septin filaments in these latter cases has been estimated in 7–9 nm (Field et al., 1996; Frazier, et al., 1998; Hsu et al., 1998). Filaments assembled from recombinant XSepA appeared as paired structures formed by what can be interpreted as two filaments of 8–9 nm in width each FIGS. 2A and 2B. If this interpretation is confirmed, the diameter of individual XSepA filaments would be consistent with that of septin filaments purified from cells. Interestingly, paired filaments of length $\geq 1500$ nm are obtained when the purified yeast septin complex is briefly dialysed from 1M KCl into a buffer of lower ionic strength. In this latter case, filaments within a doublet were spaced by a gap of 2–20 nm without sign of a bridging structure (Frazier et al. 1998). It is therefore possible that pairing is a conserved feature of septin filaments under conditions that favour elongation. Lateral association, or bundling of septin filaments has also been described in the yeast and Drosophila complexes (Field et al., 1996; Frazier et al., 1998). Similar structures in XSepA filaments FIGS. 2A and 2B have been observed. A higher degree of bundling was evident in filaments assembled from a modified version of XSepA lacking the coiled-coil domain FIGS. 2A and 2B. Thus, it is possible that although not essential for filament formation, the coiled coil domain plays a role in side-to-side filament association.

In Xenopus cell extracts, XSepA is tightly associated with other septins. In this respect, the Xenopus septin complex is similar to septin complexes already described in yeast, insects and mammals (Field et al., 1996; Frazier, et al., 1998; Hsu et al., 1998). On the other hand, since a single septin can efficiently polymerize in vitro a certain degree of redundancy between septin proteins may be expected. It is very likely, particularly in view of the high sequence homology between septins that some, if not all, of the properties described here for XSepA filaments (nucleotide-dependent assembly and disassembly, nucleation mechanism, and polarity) may be shared by the endogenous, heteromultimeric filaments. It is not known whether overexpression of a particular septin could replace for the lack of another septin polypeptide. In yeast, conditional mutations in any of the four septin genes (CDC3, 10, 11 and 12) lead to defects in cytokinesis and to loss of the remaining septins from the division site (Haarer & Pringle, (1987); Kim, Haarer & Pringle, (1991); Ford & Pringle, (1991)). However, analysis of deletion mutants has revealed that CDC10 and CDC11 are each dispensable for viability, and cells lacking CDC10 properly localize Cdc3p and Bud4p and perform cytokinesis (Frazier et al., 1998). Thus, not all the subunits in the yeast septin complex are required for septin function.

Several recent observations have called into question whether ordered filament arrays are required for septin function in budding yeast. Ultrastructural analysis of Δcdc10 and Δcdc11 cells failed to detect the presence of neck filaments, although as mentioned above, septin-dependent functions are largely maintained in Δcdc10 mutants (Frazier et al., 1998). Moreover, septin complexes purified from these mutant strains are biochemically distinct from the wild-type complex. Whereas the wild-type complex seems to assemble into filamentous structures upon dialysis from 1M KCl, mutant complexes fail to do so. Likewise, the non-essential Gin4p kinase is required for certain aspects of septin organization (Longtine et al., (1998)). In Δgin4 cells, although cytokinesis occurs normally, the organization of septins at the bud neck appears severely altered and, must likely, incompatible with the normal arrangement of the neck filaments. These data have led to the proposal that assembly of septins into ordered filament arrays is not required for septin function. It has also been suggested, based solely on the inability of Δcdc10 complexes to associate into filaments in vitro, that septin filament assembly may be dispensable for function (Field and Kellogg, 1999; Frazier et al., 1998). The evolutionary conservation of the motifs required for GTPase activity strongly suggests that this activity is required for septin function. As it has been shown, GTP binding and hydrolysis are intimately involved in filament formation. A parsimonious resolution to this paradox is that whereas the neck filament arrays are dispensable, filament assembly is nevertheless still required for septin function.

Since septins are clearly implicated in cytokinesis Hartwell et al., 1971; Neufeld et al., 1994), the results of the present invention, which establish a mechanism for septin filament assembly, provide a basis for identifying compounds that interfere with cytokinesis.

The present invention relates, in a first aspect, to a method for identifying a compound that inhibits cytokinesis, characterized in that the compound's ability to modulate the formation and/or the stability of septins filaments is determined.

The term "modulating" denotes either "partially or completely inhibiting or decreasing" or "enhancing".

Based on the finding of the invention that septin filament assembly occurs in a GTP dependent fashion, in a preferred embodiment, the compound is tested for its ability to modulate the binding of GTP to septin monomers.

In principle, any septin that has the ability to form filaments in a GTP-dependent manner, either with identical or different septin molecules, may be used, either by itself or in combination with said other septin molecules.

Such a GTP binding assay is a biochemical assay, which may be carried out according to standard protocols, as described, inter alia, by Self et al., 1995. By way of example, this assay may be carried out as follows: In a first step, the septin monomer is incubated, in the presence or absence of the test compound, with GTP that carries a radioactive label (e.g. the commercially available $\alpha$-$^{32}$P-GTP or $^3$H-GTP) or an otherwise measurable, e.g. a fluorescent label, as described, inter alia, by Hazlett et al., 1993, under conditions and for a period of time sufficient to allow saturation of GTP binding sites. The optimal assay conditions may be determined as follows: In a first step, the septin is selected, e.g.

recombinant septin A, and the desired protein concentration is established by a standard assay (e.g. the commercially available BioRad assay). In addition, a suitable buffer is selected, e.g. S-buffer, as described in the Examples. Next, time courses of GTP binding are performed using different GTP concentrations to determine the optimal conditions, i.e. nucleotide concentration and incubation time, to reach saturation. Examples for suitable assay conditions are 5 min at a septinA concentration of 1 μM, or 30 min at a septinA concentration of 20 μM at room temperature in S-buffer.

Once the assay has been established, the test compound's ability to modulate the GTP binding reaction is determined by measuring the amount of bound GTP and comparing the obtained result with that of the control reaction carried out in the absence of the test compound.

The principle of this type of assay is described in the Examples.

The assay may be performed in the high throughput format by automation of the reaction steps, including, in the case of using a radioactive assay, the separation of septin-bound and unbound GTP. In this case, a great number of compounds, e.g. from compound or natural product libraries, are applied to microtiter plates containing the reagents for the binding reaction. After the time required for GTP saturation in the control reaction (absence of test compound), the reaction solution may be filtered through a protein binding matrix, e.g. nitrocellulose, that is arranged in the same geometrical pattern as the original microtiter plate where the reaction took place, and the radioactivity retained in the filters is quantified.

To simplify the assay, the septin(s) may be immobilized on a solid matrix, either via a tag that allows for binding to a suitably modified solid support, e.g. by using a biotinylated septin and a streptavidin-coated microtiter plate. Alternatively, the unmodified septin(s) may be bound to a specially treated plastic or glass surface that allows for unspecific protein binding, e.g. a glass surface treated with 3-aminopropyltriethoxy-silane (Sigma). In this case, the separation of bound versus unbound GTP is achieved by simply washing away the unbound nucleotide and measuring the amount of label remaining on the plate.

Alternatively to GTP binding, the assay may be based on determining the compound's ability to modulate GTP hydrolysis. In principle, such an assay is carried out in a similar manner as described above for the GTP binding assay, with the difference that the test compound is added to the reaction after GTP saturation is complete (since GTP binding to septins has to occur prior to GTP hydrolysis, the assay design has to ensure that GTP binding occurs). The GTP molecule must be labeled in the gamma-phosphate group (e.g. gamma-$^{32}$P-GTP) in order to specifically detect hydrolysis. The readout, which may be done in the same way as described above for the GTP binding assay, may be, preferably, the amount of non-hydrolized GTP, or alternatively, the amount of released orthophosphate. The upscale of the assay to the high throughput format can be done according to the same principles as described above.

In the above-described assays that measure GTP binding to septins or GTP hydrolysis upon binding, the septin molecules employed may be identical or different. Preferably, the assay is carried out by using human septins, using as many different septins (some of them to be identified yet, e.g. by the Human Genome Project) as possible, either alone or in combination, in order to mimic the physiological situation as closely as possible. However, as long as not all human septins are available, the assay may conducted with septins from other organisms, preferably from vertebrates, e.g. Xenopus laevis.

Alternatively to using the full-length protein, a truncated version may be used, as long the GTPase activity is maintained, e.g. a fragment lacking the C-terminal sequence which, in the case of XseptinA has been shown to be dispensible for filament formation.

A number septins that are suitable for use in a GTP binding or hydrolysis assay are available, they have been cloned from various species. Preferably, the septins are employed as recombinant proteins obtained by expression in suitable hosts, e.g. in *E. coli* or in insect cells, according to conventional methods.

Examples for septins that may be employed are hNEDD5 (GenBank accession number D63878), PNUTL2 (GenBank accession number NM_004574) and CDCREL-1 (GenBank accession number AF006998 U07983).

Alternatively to determining a compound's effect on GTP binding or GTP hydrolysis, it may be determined whether the compound promotes or inhibits septin filament formation, or enhances or reduces the stability of septin filament.

A suitable assay comprises incubating septin molecules, which may be identical or different, and monitoring the formation of filaments, e.g. by fluorescence measurement. In such an assay, the septin monomers carry a fluorescent label whose fluorescence increases when the agent is arranged in a precise order, as it occurs e.g. upon filament assembly. An example for such a fluorescent label is a pyrene, e.g. N-(1-pyrenyl)iodoacetamide, which was described by Kouyama et al., 1981, for conjugating actin to follow polymerization. This method can be applied in the present invention to monitor septin filament formation.

A compound's modulating effect on polymerization is determined by measuring its effect on the increase of the fluorescence that is observed in a control experiment carried out in the absence of the compound.

An assay of this type can be established as follows:

The fluorescence-labeled septin molecules, either identical or different, are incubated, in the presence or absence (control sample) of the test compound, with GTP under conditions that allow polymerization in the control sample (in the case of septinA, the minimal conditions are 0.6 mg/ml septin and 0.1 mM GTP in S-buffer for 5 min) and are sufficient for a measurable increase in the fluorescent signal. The readout of the assay; which shows a test compound's effect on filament formation, is the difference in fluorescence between the test sample and the control sample.

In an alternative assay, the test compound's effect on septin filament stability can be determined by a similar method, with the difference that the test compound is added to reaction mixture after filament formation has been completed. Upon further incubation with the test compound the fluorescence will either decrease (in the case of the compound's filament destabilizing effect) or increase (in the case of the compound's filament stabilizing effect).

The above-described assays, which determine whether the compound promotes or inhibits septin filament formation, or whether it enhances or reduces the stability of septin filament, can be employed as a primary screen or, alternatively, as a secondary screen following a primary screen based on GTP binding and/or GTP hydrolysis. Such a secondary screen may be followed by a detailed characterization of the compound's effect on filament formation/stability, as assayed by standard sedimentation, fluorescence or electron microscopy procedures. The secondary assay and the subsequent filament characterization will confirm that a test compound does not only effect GTP binding/hydrolysis, but also filament formation/stability, which appears to be the septins' fundamental biological role in cytokinesis and is therefore the mechanism relevant for therapeutical intervention.

Compounds that have been identified in the above-defined screens due to their ability to modulate the nucleotide binding or hydrolysis and/or polymerization of septin monomers in vitro are candidates for drugs that affect the function of septins in vivo.

Since septins have an essential role in cell division, modulators of septin filament assembly/stability have the potential to perturb cytokinesis. In tumor cells, this effect may result in a decrease or a stop of tumor growth. In addition, inhibition of cytokinesis may cause the activation of a cell cycle arrest check point that will trigger apoptosis of the tumor cells.

By way of example, the candidate compounds can be assayed for their effect on cytokinesis and other cellular processes in tissue culture of normal or transformed cells. To test the inhibition of tumor cell proliferation, primary human tumor cells are incubated with the compound identified in the screen and the inhibition of tumor cell proliferation is tested by conventional methods, e.g. bromo-desoxy-uridine or $^3$H incorporation.

Compounds that exhibit an anti-proliferative effect in these assays may be further tested in tumor animal models and used for the therapy of tumors.

Thus, in a further aspect, the invention relates to compounds identified in the above screens for the therapy of tumors.

In addition to their role in cytokinesis, septins have been shown to be highly expressed in brain, where they are associated with molecules of the secretory pathway. Thus, the septins appear to be involved in neurosecretion events (Hsu et al., 1998; Beites et al., 1999). Modulators of septin filament assembly/stability may therefore be useful for the treatment of neurodegenerative disorders, e.g. Alzheimer's disease or Huntington disease, and stroke.

Thus, in a further aspect, the invention relates to compounds identified in the above screens for the therapy of neurodegenerative diseases.

Toxicity and therapeutic efficacy of the compounds identified as drug candidates by the method of the invention can be determined by standard pharmaceutical procedures, which include conducting cell culture and animal experiments to determine the $IC_{50}$, $LD_50$, the $ED_{50}$. The data obtained are used for determining the human dose range, which will also depend on the dosage form (tablets, capsules, aerosol sprays, ampules, etc.) and the administration route (oral, buccal, nasal, paterental or rectal). A pharmaceutical composition containing the compound as the active ingredient can be formulated in conventional manner using or more physiologically active carriers and excipients. Methods for making such formulations can be found in manuals, e.g. "Remington Pharmaceutical Sciences".

A) Schematic representation of the primary structure of XSepA

B) Coomassie-stained acrylamide gel showing affinity-purified XSepA

C, D) Time courses of GTP binding and hydrolysis by XSepA and Δcc-SepA

Figures 2A, 2B:
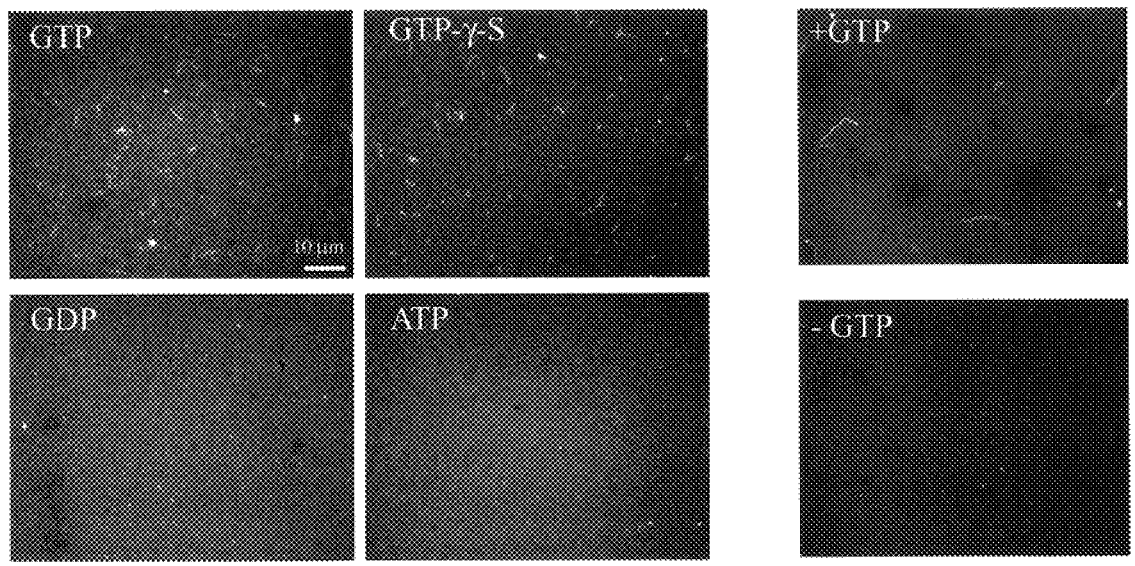

FIGS. 2A and 2B: GTP-dependent assembly of XSepA and Δcc-SepA filaments

FIGS. 3A–3D: Electron microscopy of SepA filaments
A–D: XSepA filaments
E: Δcc-SepA filaments FIGS. 4A–4C: Quantitative analysis of XSepA polymerization in the presence of GTP and GTP-γ-S FIGS. 5A and 5B: Polarity of filament growth In the Examples, the following materials and methods were used:

i) Cloning, Expression and Purification of XSepA

Partial septin cDNAs were amplified from Xenopus oocyte RNA using degenerate oligonucleotides as primers. The PCR products were cloned in pBlueScript, sequenced, and those encoding septin fragments used as probes to screen a lambda-zap Xenopus oocyte library. A full-length XSepA clone was obtained and the coding sequence (or the coding sequence minus the predicted coiled-coil domain which comprises aminoacids 309–356 (Lupas et al., 1991) was sub-cloned in an IMPACT T7 vector (NEB) as an N-terminal in-frame fusion with the intein-CBD (chitin-binding domain) coding sequence. BL21(DE3) cells (Stratagene) containing the XSepA-intein construct were grown in LB medium until log phase and protein expression induced with IPTG overnight at 25° C. Harvested cells were lysed by sonication in 20 mM Tris pH 8.0, 20 mM NaCl, 20% glycerol, 1 mM $MgCl_2$, 0.1% Triton X-100. Clarified extracts were loaded into a chitin-agarose column and affinity purification performed according to the manufacturer's instructions. After DTT-induced cleavage of the intein-CBD moiety, the protein was eluted from the column, peak fractions pooled and dyalysed against the above buffer containing 5 mM DTT (S-buffer), and the dialysate concentrated in an Ultrafree filter unit (Millipore) to a final XSepA concentration of 2–4 mg/ml.

For biotin labeling, chitin beads loaded with XSepA-intein were equilibrated in 20 mM Hepes pH 7.5 and incubated with 25 μg/ml biotin XX-NHS ester (Molecular Probes) for 1 h at 4° C. The beads were then repacked, washed with S-buffer and cleavage induced overnight as above.

ii) GTP Binding and Hydrolysis Assays

For GTP binding, 1 μM of XSepA (or Δcc-SepA) in S-buffer was incubated with 0.1 mg/ml BSA, 5 mM $MgCl_2$ and 4.4 μM $^3$H-GTP (4.60 Ci/mmol, 1 mCi/ml; Amersham). At time intervals, aliquots of the reaction were diluted in cold wash buffer (20 mM Tris pH 8.0, 50 mM NaCl, 5 mM $MgCl_2$) and filtered through pre-wetted nitrocellulose circles (Schleicher and Schuell) Filters were washed with 10 ml of wash buffer, dried, and the retained radioactivity quantified in a scintillation counter.

For GTP hydrolysis, septin protein was incubated with GTP as above, except that 100 nM [α-$^{32}$P]GTP (800 Ci/mmol, 10 mCi/ml) was used. At time intervals, 2 μl aliquots were diluted in 18 μl SDS 1%, EDTA 20 mM, heated at 65° C. for 10 min, and 1 μl spotted on a PEI-cellulose plate (Macherey-Nagel). Plates were developed in 1 M LiCl and air-dried. GTP and GDP spots were detected by phosphorimaging. Nucleotide $R_f$ values were confirmed by visualising cold standards with UV light.

iii) Filament Immunofluorescence and Sedimentation Assays

Polymerization reactions were carried out in S-buffer in the presence of 5 mM $MgCl_2$ and GTP, GTP-γ-S, GDP or ATP (Gibco). Before nucleotide addition, all samples were pre-cleared in an ultracentrifuge (see below). Aliquots of the reaction were diluted to a final septin concentration of 3.3 μg/ml, and 100 μl drops spotted on glass coverslips for 1 min. Before use, coverslips were soaked with an acetone solution of 0.5% 3-aminopropyltriethoxy-silane (Sigma), washed in acetone and air-dried. Following sample application, the coverslips were washed with 2 ml S-buffer, fixed in cold methanol for 10 min and stained with a polyclonal rabbit antibody raised against an N-terminal peptide of XSepA (M. Glotzer and T. Hyman, in preparation). Secondary antibodies were DTAF-coupled anti-rabbit (Dianova). Images were acquired using a Zeiss Axioplan II microscope and Adobe Photoshop software. Processing and analysis of immunofluorescence images was performed on a Macintosh computer using the public domain NIH Image program (developed at the U.S. National Institutes of Health and available at http://rsb.info.nih.gov/nih-image). Thresholded binary images were generated, and particle length was obtained by measuring the major axis of the best fitting ellipse. Particles with length <0.4 μm were not included in the analysis. Although filaments tended to be straight, this procedure results in underestimation of the length of curved filaments. For sedimentation assays, 20 μl polymerization reactions containing 1 mg/ml septin were pre-cleared in an ultracentrifuge at 279000×g for 15 min at 4° C. Precleared samples were incubated with nucleotide at room temperature for 30 min and spun through a 50% glycerol cushion at 279000×g for 15 min at 25° C.

iv) Electron Microscopy

Following incubation with GTP, polymerization reactions were diluted to a septin concentration of 0.4 mg/ml in S-buffer and applied to carbon-coated grids. The grids were stained with two drops of 1% uranyl acetate and viewed in a JEOL 1210 electron microscope.

v) Polarity Assay

2 μl of a 30-min polymerization reaction were diluted into 18 μl of 0.3 mg/ml biotin-XSepA in S-buffer supplemented with 0.1 mM GTP, to yield a total septin concentration of 0.4 mg/ml. At different times, aliquots-of the reaction were diluted 100-fold and processed for immunofluorescence as described. Coverslips were double-stained with anti-XSepA antibody (as above) and DTAF-Streptavidin (Dianova).

EXAMPLE 1 a) Expression of Xenopus Septin A (XSepA) in *E. coli*

Figure 1A:
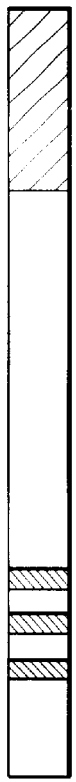
FIGS. 1A–1D.

To obtain large amounts of septin protein, Xenopus septin A (XSepA) was expressed in *E. coli* and the protein purified by column chromatography taking advantage of a self-cleavable affinity tag. The purity of the column eluate exceeded 90% as judged by Coomassie stained acrylamide gels (FIG. 1B: Coomassie-stained acrylamide gel showing affinity-purified XSepA. The major band corresponds to the expected XSepA molecular weight of 41 KDa.) Like all known septins, XSepA contains a P-loop motif and other sequences characteristic of GTP binding proteins (scheme in FIG. 1A: Schematic representation of the primary structure of XSepA. The P-loop and other GTP-binding motifs are featured as vertical thick lines. The coiled-coil motif, deleted in the Δcc-SepA construct, comprises aminoacids 309–356 (black bar)).

b) Testing the Ability of Recombinant XSepA to Bind Guanine Nucleotide

Figure 1C:
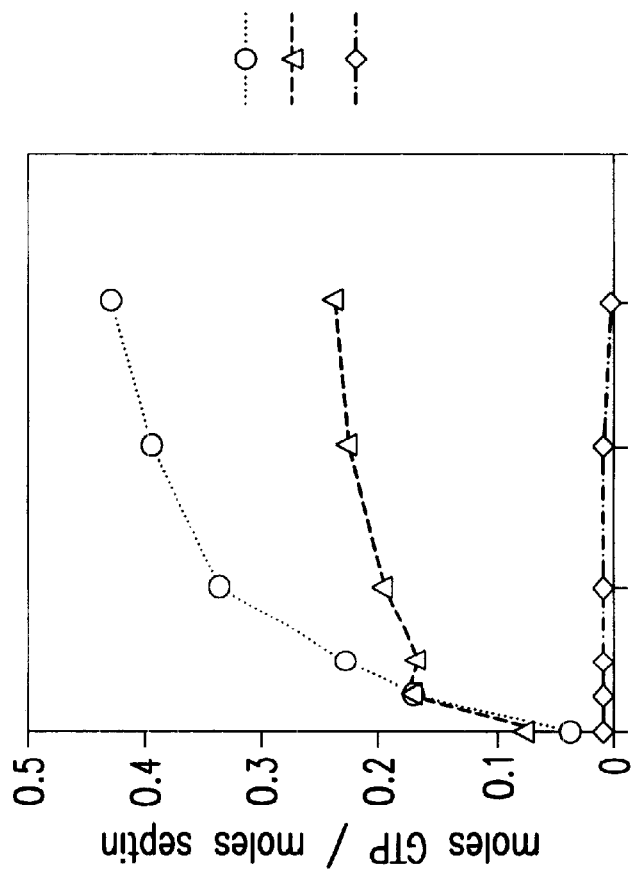
Figure 1B:
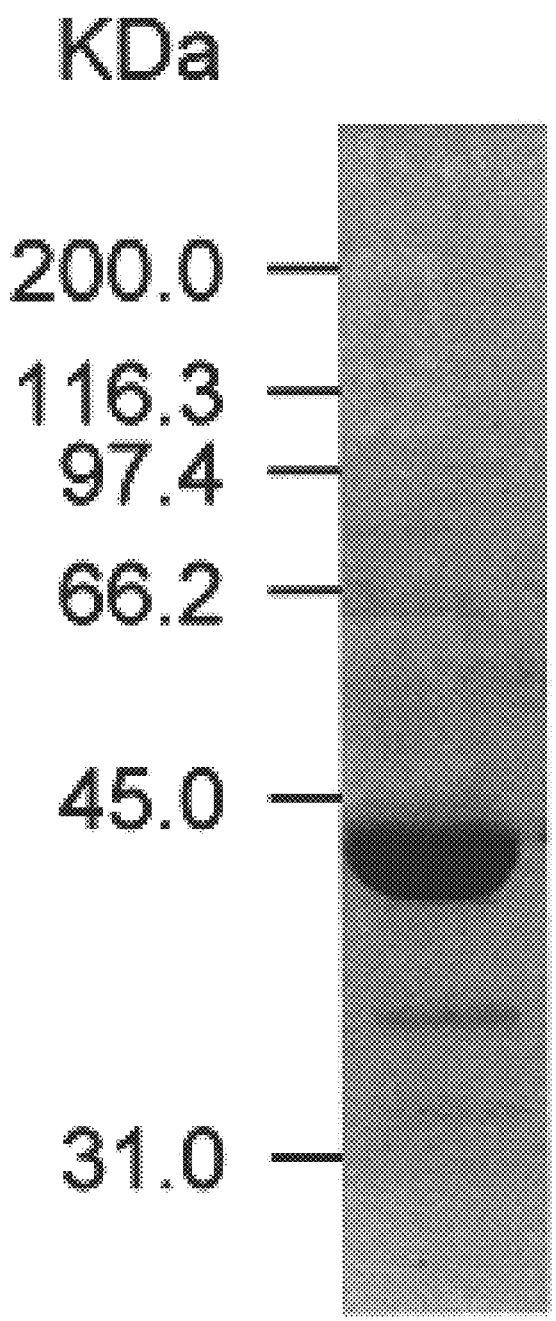

The ability of recombinant XSepA to bind guanine nucleotide was tested by using a filter binding assay. Recombinant XSepA was able to bind [$^3$H]GTP with a half-time ($t_{1/2}$) of 10 minutes, whereas the BSA control showed no detectable binding (FIG. 1C). Binding is specific for GTP, since only cold GTP, but not ATP or GDP, was able to compete with the radiolabeled guanine nucleotide (data not shown). A GTP binding plateau of 0.4–0.5 moles GTP/moles of XSepA was typical for these experiments, indicating that a fraction of the recombinant protein is not competent for nucleotide binding.

Figure 1D:
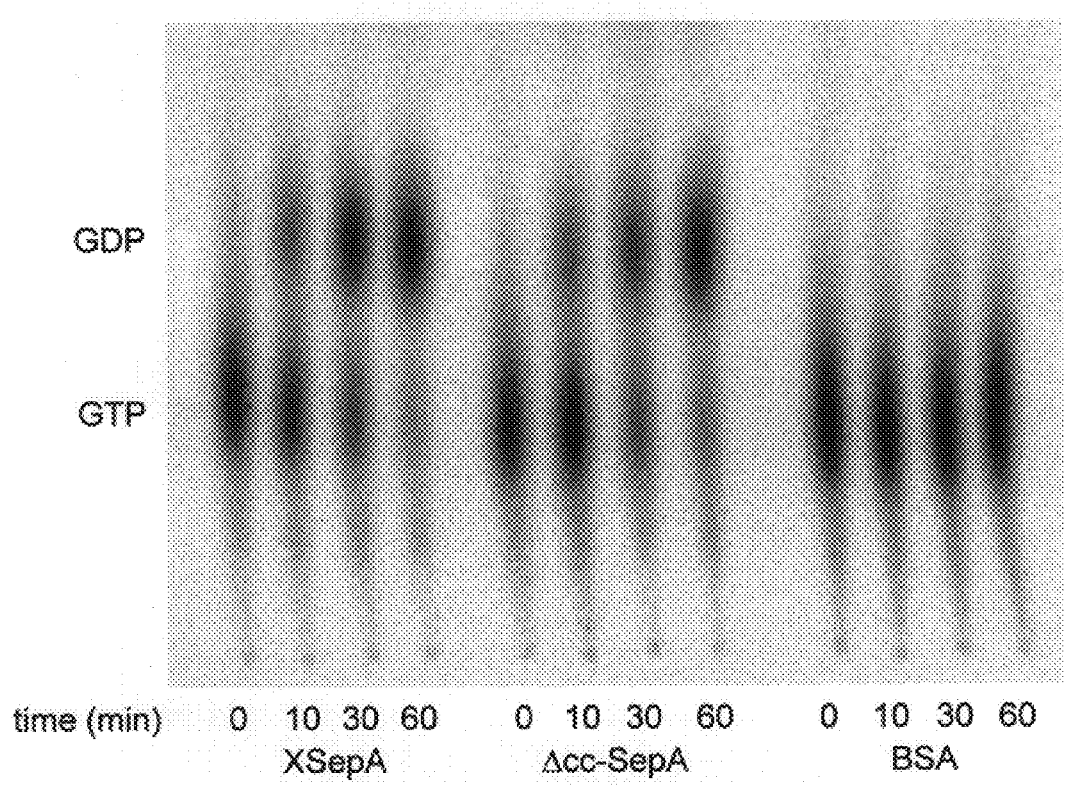

To assay for GTP hydrolysis, XSepA was incubated with limiting amounts of [α-$^{32}$P]GTP and the production of radioactive GDP was followed by thin layer chromatography. GTP binding and hydrolysis occurred with relatively fast kinetics: when a limiting concentration of nucleotide was used, a maximum of nucleotide binding was essentially complete within 5 minutes (not shown) whereas GTP hydrolysis showed a $t_{1/2}$ of ca. 20 minutes (FIG. 1D). FIGS. 1C and 1D show time courses of GTP binding and hydrolysis by XSepA and Δcc-SepA. Recombinant protein (1 μM) was incubated with an excess of [$^3$H]GTP to quantify nucleotide binding, or with sub-stoichiometric amounts of [α-$^{32}$P]GTP to detect nucleotide hydrolysis. (C) GTP binding as determined by a filter-binding assay. (D) TLC plate showing generation of radioactive GDP from GTP. Aliquots of the reaction were quenched in a denaturing solution at the indicated time, and the nucleotide content was resolved by TLC. BSA (0.1 mg/ml) was used as a negative control in both experiments.)

EXAMPLE 2 a) Analysis of the Regulation of Septin Filament Formation

Filament forming proteins like actin, tubulin and FtsZ polymerize in a nucleotide-dependent fashion. To test whether septin filament assembly is regulated by a similar mechanism, XSepA was incubated with GTP (or its slowly hydrolyzable analogue GTP-γ-S) for 30 minutes and spotted onto glass coverslips. After the coverslips were fixed and stained with anti-XSepA antibody, filamentous structures of up to 7 μm in length were observed. This was not the case in control experiments where ATP or GDP were used instead of GTP. FIGS. 2A and 2B depict the GTP-dependent assembly of XSepA and Δcc-SepA filaments. Top panels: Immunostainings of septin preparations (1 mg/ml) incubated with 0.1 mM of the indicated nucleotide for 30 min and diluted in S-buffer prior to fixation. Filamentous structures are observed with both full-length (A) and Δcc-SepA (B) only in the presence of GTP or GTP-γ-S. Bottom panels: Identical reactions were centrifuged through a 50% glycerol cushion at 279000×g for 15 min. Supernatants (S) and pellets (P) were collected and resolved by gel electrophoresis.

The GTP-dependent formation of high molecular weight structures could also be followed by sedimentation. After incubation with nucleotide, septin preparations were spun through glycerol cushions and the supernatants and pellets loaded separately in an acrylamide gel. The sedimentable fraction of septin increased significantly after incubation with GTP or GTP-γ-S, as shown in FIG. 2B. The presence of guanine nucleotide is therefore sufficient to induce assembly of XSepA into filamentous structures.

b) Analysis of the Role of the Septin Coiled-coil Domain for Filament Formation

Many (but not all) of the known septins contain C-terminal sequences predicted to form coiled-coil domains. To investigate whether the coiled coil is required in filament assembly, an XSepA construct lacking this domain was generated. The encoded protein, Δcc-SepA, was expressed and purified as described for the full-length septin. The truncated septin maintained GTPase activity, albeit with a reduced GTP-binding efficiency FIGS. 1C and 1D. This could indicate that a larger fraction of the truncated protein fails to fold correctly in the bacterial cell as compared to the full-length septin. Importantly, purified Δcc-SepA was able to assemble into filaments in the presence of GTP as judged by immunofluorescence (FIG. 2B). Moreover, co-assembly between full-length XSepA and a biotinylated form of Δcc-SepA was also observed, using anti-XSepA antibody in conjunction with fluorophore-coupled streptavidin (data not shown). Δcc-SepA filaments were relatively less abundant than XSepA filaments, even though they were polymerized under equivalent conditions (compare GTP panels in FIGS. 2A and 2B). Centrifugation experiments showed that sedimentation efficiency was reduced by a factor of 4 (FIG. 2B, bottom panel). Thus, the filament formation ability of XSepA is diminished, but not abolished, upon deletion of the coiled coil domain.

EXAMPLE 3
Investigation of XSepA Filament Structure

To gain information on the structure of XSepA filaments, the products of the polymerization reaction were analysed using electron microscopy (EM). GTP-assembled XSepA filaments were adsorbed to carbon-coated grids and processed for negative staining. FIGS. 3A–3E show electron microscopy of XSepA (A–D) and Δcc-SepA filaments (E). (A) Filaments adsorbed to the grid 5 minutes after GTP addition. In (B) a higher magnification of the filament at the left is shown, that appears to be composed of two thinner (8–9 nm) filaments in close association. (C) Filament doublets after 30 minutes polymerization. (D) A region of the grid where 20 nm-wide doublets are seen in proximity of a thicker filament bundle. (E) Δcc-SepA filaments with different degrees of lateral aggregation. Scale bars, 200 nm in A, D and E; 50 nm in B and C.

Figure 3A:
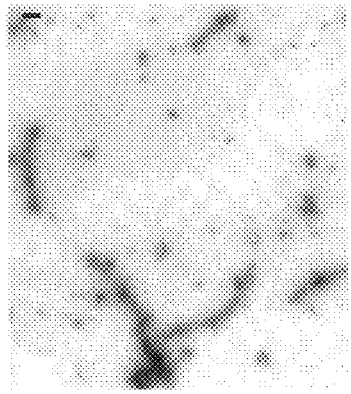
Figure 3B:
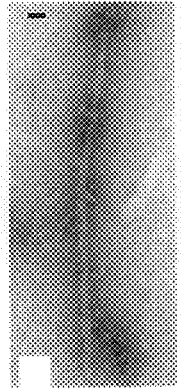
Figure 3C:
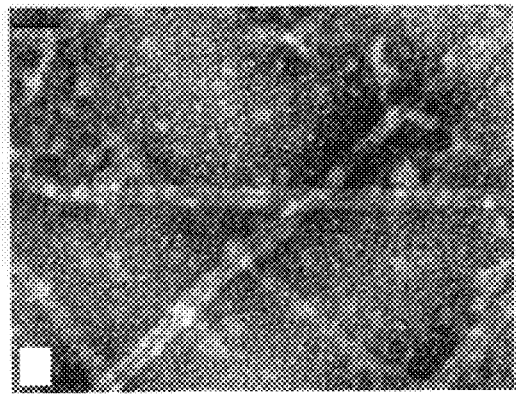
Figure 3D:
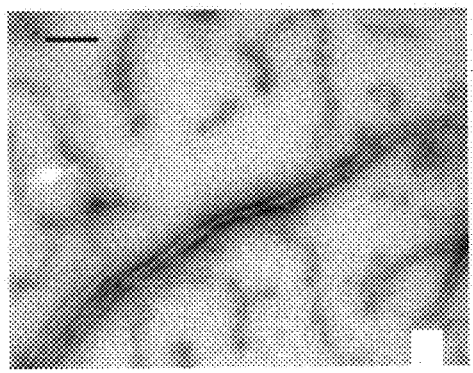
Figure 3E:
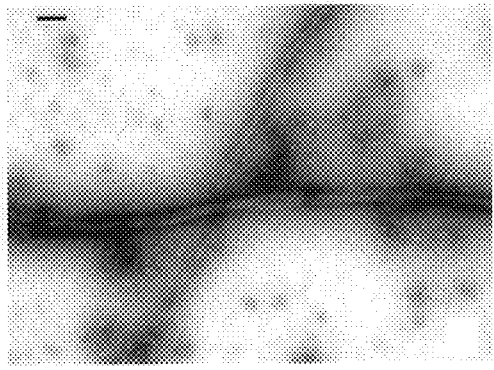

Short filaments (length between 200 and 1000 nm) could be detected in reactions that had been incubated with GTP for 5 minutes (FIGS. 3A and 3B), whereas more extended incubation periods resulted in filaments ≧1000 nm long. The width of the filaments was estimated in 20–22 nm. A narrow region of electron-dense material was visible along the filament lengths (FIGS. 3B and 3C), suggesting that the 20 nm-wide structures are composed of two 8–9 nm wide filaments in close apposition. Lateral association of several of these paired structures was also observed, particularly upon 10 or more minutes incubation with nucleotide (FIG. 3D). Filaments composed of Δcc-SepA were also examined by EM. Interestingly, a higher degree of bundling was evident in this case even at short incubation times (FIG. 3E) and only few thinner filaments (30–40 nm in width) were detected.

EXAMPLE 4
Investigation of the Polymerization Mechanism of XSepA

Figure 4B:
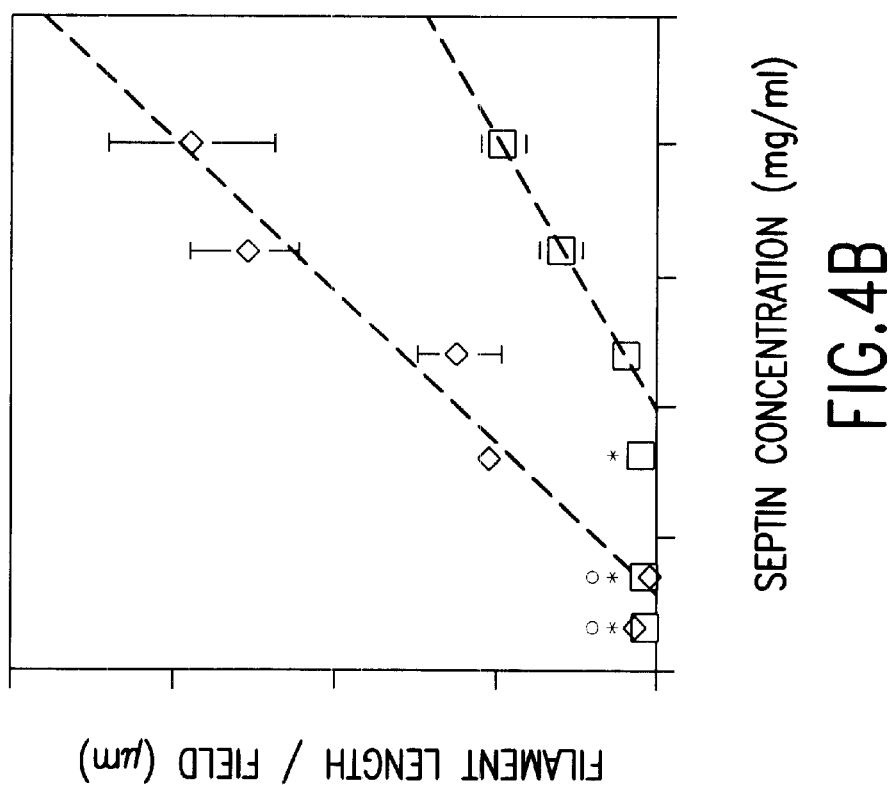
Figure 4A:
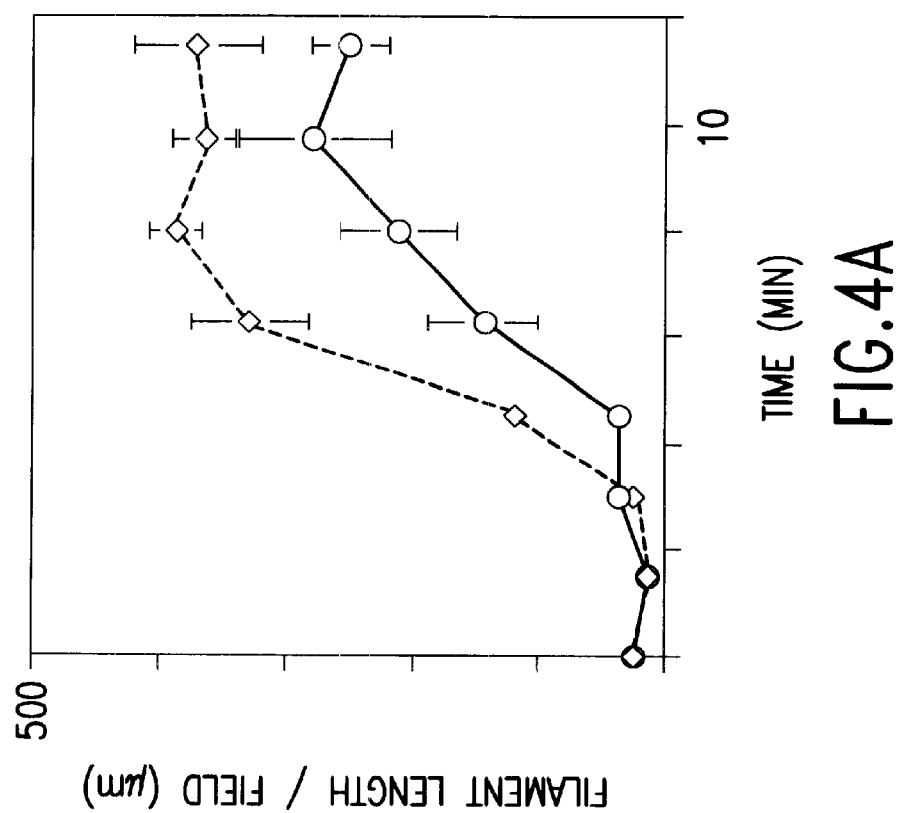
Figure 4C:
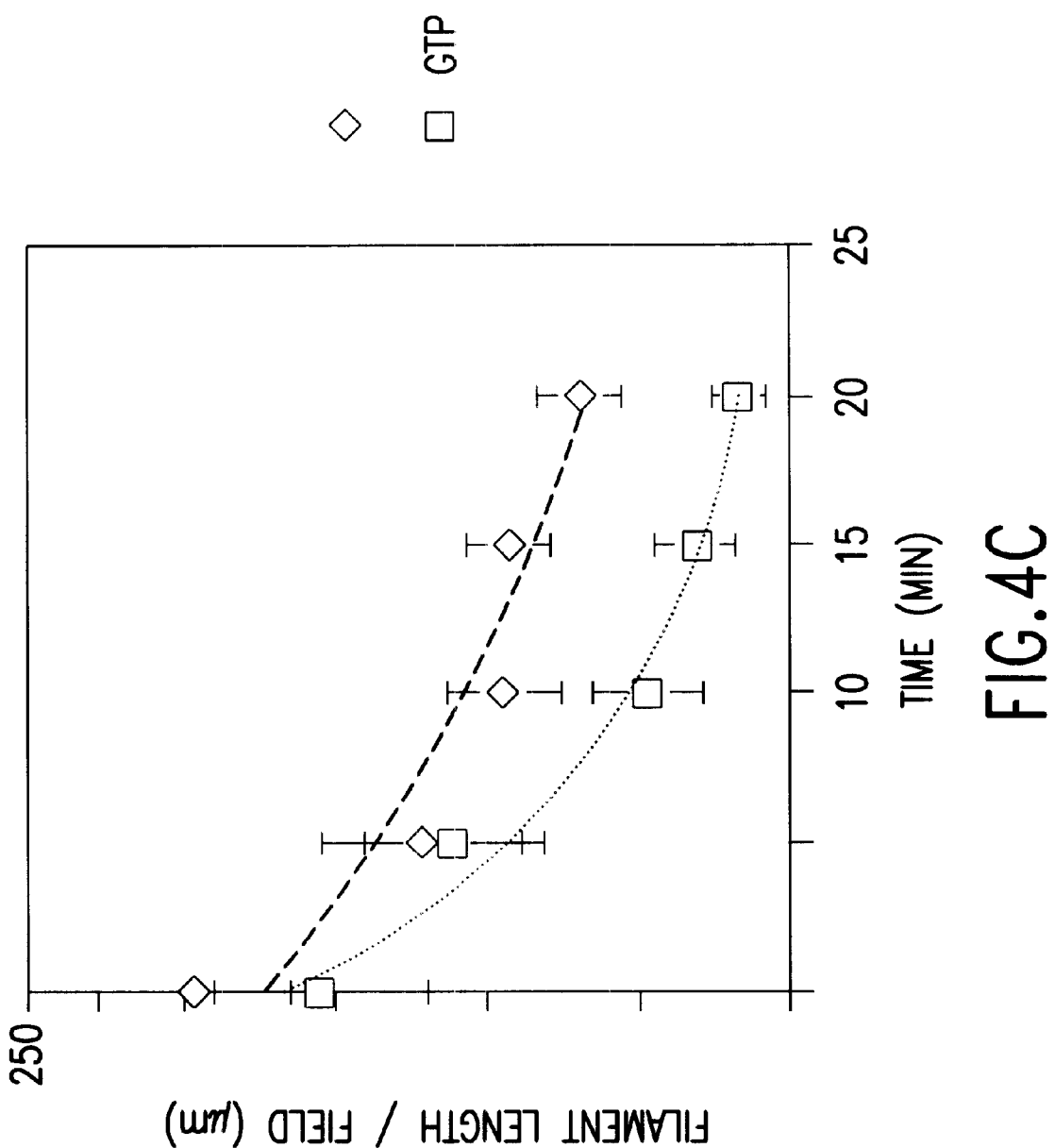

To gain insight into the polymerization mechanism of XSepA, the kinetics of the filament formation reaction was followed using immunofluorescence microscopy. At different times after GTP addition, aliquots of septin protein were processed for immunofluorescence as already described. For each time point, individual septin filaments were counted and their lengths measured. The length of all the filaments present in a field was added, and the result (proportional to the polymer mass) was plotted against time. Quantitative analysis of XSepA polymerization in the presence of GTP and GTP-γ-S is shown in FIGS. 4A–4C. Immunofluorescence images were acquired as described and the length of the filaments was measured (see Methods section). The relative polymer mass was obtained by adding the length of all the filaments present in a field. Each point represents data from four random fields. Only filaments of ≧400 nm in length were considered in the analysis. (A) Time course of filament assembly. At different times following nucleotide addition to 0.1 mM (t=0 min) aliquots of a reaction containing 1 mg/ml XSepA were diluted 300-fold and spotted on coverslips for 1 min before washing and fixation. (B) Determination of the critical concentration for polymerization. Separate reactions were set up with increasing concentrations of XSepA and incubated with 1 mM GTP. Polymer content was determined after 30 min incubation. Before spotting on coverslips, each reaction was diluted proportionally in order to normalize the protein concentration. Asterisks (*) and open circles (○) indicate concentrations at which no filaments were observed in the presence of GTP or GTP-γ-S, respectively. (C) Time course of filament disassembly. 30 min after nucleotide addition, polymerization reactions containing 1 mg/ml XSepA were diluted (t=0) 300-fold in S-buffer supplemented with nucleotide. Aliquots of diluted protein were subsequently processed for immunofluorescence without further dilution. In (B) and (C) a curve was fitted to the data points where filaments were detected.

The polymerization curve (continuous line in FIG. 4A) reveals an initial slow phase where no filaments are detected. After this lag phase, a rapid polymerization phase was observed where many filaments suddenly appear. The presence of a lag phase is indicative of nucleation. Finally, an equilibrium of polymer mass is reached. During this last phase, filament length redistribution occurs in which the number of short filaments decreases while the mean length of the population increases (data not shown). These polymerization kinetics are consistent with a nucleation mechanism of filament assembly, as opposed to simple linear polymerization (Cantor et al., 1980).

A nucleated polymer can be in equilibrium with its monomeric form only above a certain concentration value known as the "critical concentration". Below the critical concentration, nucleation can not occur and only monomers (and a small number of short oligomers) can exist (Cantor et al., 1980). The relationship between degree of polymerization and protein concentration of XSepA (FIG. 4B, continuous line) was investigated. XSepA at different concentrations was incubated for 30 minutes with GTP. Equal amounts of protein were spotted on glass coverslips and the relative polymer mass quantified as described above. Consistent with a nucleated polymerization mechanism, filaments were observed only at a septin concentration of 0.6 mg/ml or higher, while the polymer mass increased linearly above 0.6 mg/ml.

EXAMPLE 5
Analysis of the Role of GTP Hydrolysis in Septin Filament Formation

To address the role of GTP hydrolysis in septin filament formation, the polymerization kinetics of XSepA in the presence of a slowly hydrolysable GTP analogue, GTP-γ-S, was studied. The use of GTP-γ-S in the polymerization reaction resulted in a shortening in the length of the lag phase from 5 to 3 minutes (compare dashed and continuous lines in FIG. 4A). The critical concentration was also reduced from 0.5 to 0.2 mg/ml (compare the respective lines in FIG. 4B). These results suggest that nucleotide hydrolysis might destabilize the nascent polymer. To investigate directly whether nucleotide hydrolysis promotes disassembly, filaments assembled with GTP or GTP-γ-S were diluted 600-fold into buffer and depolymerization rates were determined. After 20 min the depolymerization was essentially complete in the GTP reaction, whereas GTP-γ-S assembled filaments were still present at ca. 30% of their initial level (FIG. 4C). Therefore, GTP-γ-S assembled filaments are more resistant to dilution-induced depolymerization. From these experiments, it was conclude that GTP binding promotes filament assembly, whereas GTP hydrolysis destabilizes the filaments and facilitates depolymerization.

Figure 5A:
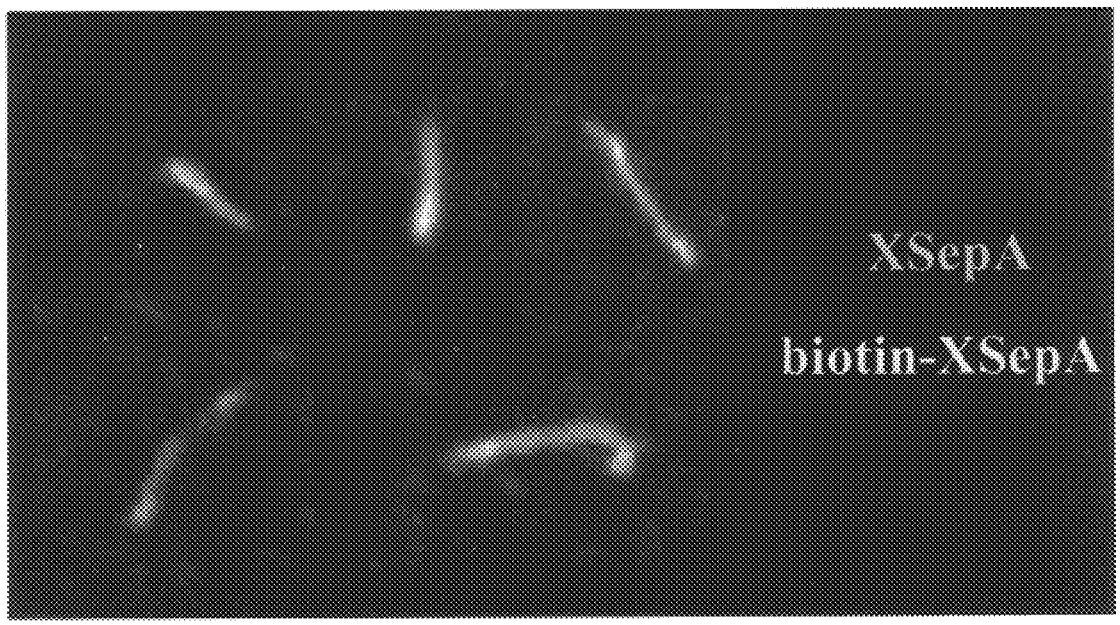
Figure 5B:
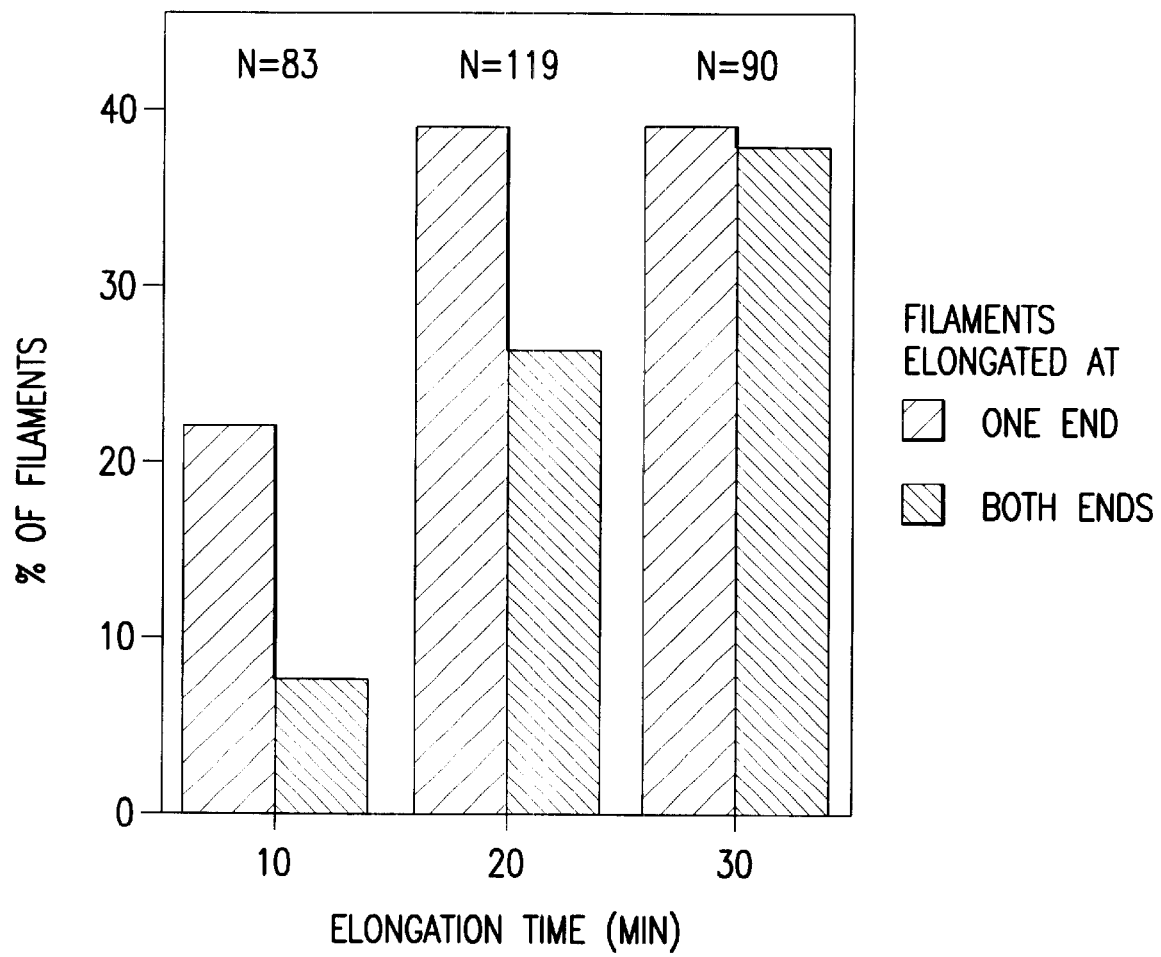

Actin filaments and microtubules display different polymerization kinetics at their two ends. To test whether XSepA filaments show similar properties, filaments were diluted into biotin-conjugated monomeric septin. The final protein concentration was just below the critical concentration, so that de novo filament formation can not occur, but pre-existing filaments can elongate and incorporate the biotinylated monomer. Such elongated filaments were double stained with anti-XSepA antibody and streptavidin was fluorophore-coupled to visualise the biotin moiety. FIGS. 5A and 5B show the polarity of septin filament growth. XSepA filaments assembled with GTP for 30 min were diluted in S-buffer containing monomeric biotin-XSepA and GTP. At 10 min intervals after mixing, the reaction was processed for immunofluorescence. In (A) are shown filaments stained with anti-XSepA antibody (green) and Cy3-streptavidin (red) to visualize the biotinylated protein incorporated at the end of the filaments. To determine whether the two filament ends differ in their polymerization kinetics, the number of filaments elongated at one or two ends was scored at different times and the result plotted in (B). Images corresponding to five or six random fields were acquired for each time point. N indicates the number of filaments scored at each time point. Filaments that appeared bundled or with biotin-containing stretches at mid-length (indicative of end-to-end fusion) were not included in the analysis. These two classes represented from 15% to 30% of the total filament population and their number increased with the elongation time.

Biotin incorporation at the filament ends was detected 10 minutes after addition of the labeled septin (FIG. 5A) and increased with the incubation time. Elongated ends were rather short in length, presumably because the concentration of monomer was limiting. Accurate measurement of elongated segments was therefore not possible because of the resolution limit of light microscopy. However, it was found that the majority of labeled filaments elongated at only one end. Ten minutes after dilution into labeled monomer (FIG. 5B) the ratio between filaments elongated at one end versus those elongated at both ends was 3:1 (N=83). This difference diminished with time to a ratio of 1:1, indicating that both ends are competent for elongation. These data can be interpreted as supportive of the view that XSepA filaments are polar structures, in the sense that they grow differently at their two ends.

REFERENCES

1. Cooper, J. A. & Kiehart, D. P. J Cell Biol 134, 1345–8 (1996).
2. Longtine, M. S., et al. Curr Opin Cell Biol 8, 106–19 (1996).
3. Field, C. M. & Kellogg, D. Trends Cell Biol 9, 387–94 (1999).
4. Hartwell, L. H. Exp Cell Res 69, 265–76 (1971).
5. Byers, B. & Goetsch, L. J Cell Biol 69, 717–21 (1976).
6. Neufeld, T. P. & Rubin, G. M. Cell 77, 371–9 (1994).
7. Kinoshita, M., et al. Genes Dev 11, 1535–47 (1997).
8. Xie, H., Surka, M., Howard, J. & Trimble, W. S. Cell Motil Cytoskeleton 43, 52–62 (1999).
9. Chant, J., Mischke, M., Mitchell, E., Herskowitz, I. & Pringle, J. R. J Cell Biol 129, 767–78 (1995).
10. Sanders, S. L. & Herskowitz, I. J Cell Biol 134, 413–27 (1996).
11. DeMarini, D. J., et al. J Cell Biol 139, 75–93 (1997).
12. Bi, E., et al. J Cell Biol 142, 1301–12 (1998).
13. Field, C. M., et al. J Cell Biol 133, 605–16 (1996).
14. Frazier, J. A., et al. J Cell Biol 143, 737–49 (1998).
15. Hsu, S. C., et al. Neuron 20, 1111–22 (1998).
16. Beites, C. L., Xie, H., Bowser, R. & Trimble, W. S. Nat Neurosci 2, 434–9 (1999).
17. Cantor, C. & Schimmel, P. Biophysical Chemistry Part 1: The Conformation of Biological Macromolecules (W. H. Freeman, New York, 1980).
18. Mitchison, T. J. Mol Biol Cell 3, 1309–15 (1992).
19. Mitchison, T. & Kirschner, M. Nature 312, 232–7 (1984).
20. Kirschner, M. Mitchison, T. Cell 45, 329–42 (1986).
21. Haarer, B. K. & Pringle, J. R. Mol Cell Biol 7, 3678–87 (1987).
22. Kim, H. B., Haarer, B. K. & Pringle, J. R. J Cell Biol 112, 535–44 (1991).
23. Ford, S. K. & Pringle, J. R. Dev Genet 12, 281–92 (1991).
24. Longtine, M. S., Fares, H. & Pringle, J. R. J Cell Biol 143, 719–36 (1998).
25. Lupas, A., Van Dyke, M. & Stock, J. Science 252, 1162–4 (1991).
26. Kouyama T. et al. (1981).Eur J Biochem. 114(1): 33–8
27. Self, A. J. and A. Hall (1995),Methods in Enzymology 256, 67–76
28. Hazlett T L, et al. (1993). Biochemistry. Dec 14; 32(49):13575–83.

What is claimed is:

1. A method for identifying compounds that modulate cytokinesis comprising:
    (a) in a control system, incubating septin molecules under conditions that allow polymerization of the septin molecules, wherein said conditions include the presence of GTP;
    (b) in a test system, incubating septin molecules under the conditions of (a), wherein said incubation occurs in the presence of test compounds;
    (c) measuring GTP hydrolysis and/or binding in (a) and (b); and
    (d) comparing the GTP hydrolysis and/or binding in (a) with that of (b), wherein an enhancement of GTP hydrolysis and/or binding or a decrease in GTP hydrolysis and/or binding demonstrates that said test compound has the ability to modify cytokinesis.

2. The method of claim 1, wherein GTP hydrolysis is compared.

3. The method of claim 1, wherein GTP binding is compared.

4. The method of claim 1, wherein said GTP carries a radioactive label.

5. The method of claim 1, wherein said septin molecules are different.

6. The method of claim 1, wherein said septin molecules are immobilized on a solid matrix.

7. The method of claim 6, wherein said septin molecules are immobilized to a steptavidin-coated matrix.

8. The method of claim 1, comprising measuring the amount of non-hydrolyzed GTP or the amount of released orthophosphate.

9. A method for identifying compounds that modulate cytokinesis comprising:
    (a) in a system, incubating septin molecules under conditions that allow polymerization of the septin molecules, wherein said conditions include the presence of GTP;
    (b) measuring GTP hydrolysis and/or binding in (a);
    (c) adding test compounds to said system (a) after polymerization;
    (d) measuring GTP hydrolysis and/or binding in said system after step (c); and
    (e) comparing the GTP hydrolysis and/or binding in (b) with that of (d), wherein an enhancement of GTP hydrolysis and/or binding or a decrease in GTP hydrolysis and/or binding demonstrates that said test compound has the ability to modify cytokinesis.

10. The method of claim 9, wherein GTP hydrolysis is compared.

11. The method of claim 9, wherein GTP binding is compared.

12. The method of claim 9, wherein said GTP carries a radioactive label.

13. The method of claim 9, wherein said septin molecules are different.

14. The method of claim 9, wherein said septin molecules are immobilized on a solid matrix.

15. The method of claim 14, wherein said septin molecules are immobilized to a streptavidin-coated matrix.

16. The method of claim 9, comprising measuring the amount of non-hydrolyzed GTP or the amount of released orthophosphate.

17. A method for identifying compounds that inhibit cytokinesis comprising:
   (a) in a control system, incubating septin molecules under conditions that allow polymerization of the septin molecules, wherein said conditions include the presence of GTP;
   (b) in a test system, incubating septin molecules under the conditions of (a), wherein said incubation occurs in the presence of test compounds;
   (c) measuring GTP hydrolysis and/or binding in (a) and (b); and
   (d) comparing the GTP hydrolysis and/or binding in (a) with that of (b), wherein a decrease of GTP hydrolysis and/or binding demonstrates that said test compound has the ability to inhibit cytokinesis.

18. The method of claim 17, wherein GTP hydrolysis is compared.

19. The method of claim 17, wherein GTP binding is compared.

20. The method of claim 17, wherein said GTP carries a radioactive label.

21. The method of claim 17, wherein said septin molecules are different.

22. The method of claim 17, wherein said septin molecules are immobilized on a solid matrix.

23. The method of claim 22, wherein said septin molecules are immobilized to a streptavidin-coated matrix.

24. The method of claim 17, comprising measuring the amount of non-hydrolyzed GTP or the amount of released orthophosphate.

25. A method for identifying compounds that enhance cytokinesis comprising:
   (a) in a control system, incubating septin molecules under conditions that allow polymerization of the septin molecules, wherein said conditions include the presence of GTP;
   (b) in a test system, incubating septin molecules under the conditions of (a), wherein said incubation occurs in the presence of test compounds;
   (c) measuring GTP hydrolysis and/or binding in (a) and (b); and
   (d) comparing the GTP hydrolysis and/or binding in (a) with that of (b), wherein an enhancement of GTP hydrolysis and/or binding demonstrates that said test compound has the ability to enhance cytokinesis.

26. The method of claim 25, wherein GTP hydrolysis is compared.

27. The method of claim 25, wherein GTP binding is compared.

28. The method of claim 25, wherein said GTP carries a radioactive label.

29. The method of claim 25, wherein said septin molecules are different.

30. The method of claim 25, wherein said septin molecules are immobilized on a solid matrix.

31. The method of claim 30, wherein said septin molecules are immobilized to a streptavidin-coated matrix.

32. The method of claim 25, comprising measuring the amount of non-hydrolyzed GTP or the amount of released orthophosphate.

33. A method for identifying compounds that inhibit cytokinesis comprising:
   (a) in a system, incubating septin molecules under conditions that allow polymerization of the septin molecules, wherein said conditions include the presence of GTP;
   (b) measuring GTP hydrolysis and/or binding in (a);
   (c) adding test compounds to said system (a) after polymerization;
   (d) measuring GTP hydrolysis and/or binding in said system after step (c); and
   (e) comparing the GTP hydrolysis and/or binding in (b) with that of (d), wherein a decrease in GTP hydrolysis and/or binding demonstrates that said test compound has the ability to inhibit cytokinesis.

34. The method of claim 33, wherein GTP hydrolysis is compared.

35. The method of claim 33, wherein GTP binding is compared.

36. The method of claim 33, wherein said GTP carries a radioactive label.

37. The method of claim 33, wherein said septin molecules are different.

38. The method of claim 33, wherein said septin molecules are immobilized on a solid matrix.

39. The method of claim 38, wherein said septin molecules are immobilized to a streptavidin-coated matrix.

40. The method of claim 33, comprising measuring the amount of non-hydrolyzed GTP or the amount of released orthophosphate.

41. A method for identifying compounds that enhance cytokinesis comprising:
   (a) in a system, incubating septin molecules under conditions that allow polymerization of the septin molecules, wherein said conditions include the presence of GTP;
   (b) measuring GTP hydrolysis and/or binding in (a);
   (c) adding test compounds to said system (a) after polymerization;
   (d) measuring GTP hydrolysis and/or binding in said system after step (c); and
   (e) comparing the GTP hydrolysis and/or binding in (b) with that of (d), wherein an enhancement of GTP hydrolysis and/or binding demonstrates that said test compound has the ability to enhance cytokinesis.

42. The method of claim 41, wherein GTP hydrolysis is compared.

43. The method of claim 41, wherein GTP binding is compared.

44. The method of claim 41, wherein said GTP carries a radioactive label.

45. The method of claim 41, wherein said septin molecules are different.

46. The method of claim 41, wherein said septin molecules are immobilized on a solid matrix.

47. The method of claim 46, wherein said septin molecules are immobilized to a streptavidin-coated matrix.

48. The method of claim 41, comprising measuring the amount of non-hydrolyzed GTP or the amount of released orthophosphate.

* * * * *